United States Patent [19]

Addor et al.

[11] 4,322,422

[45] Mar. 30, 1982

[54] OXALYLATED AMIDINOHYDRAZONES, METHOD FOR PREPARING SAME AND USE AS INSECT AND FIRE ANT CONTROL AGENTS

[75] Inventors: Roger W. Addor, Pennington; Thomas W. Drabb, Jr., Trenton, both of N.J.

[73] Assignee: American Cyanamid Co., Stamford, Conn.

[21] Appl. No.: 149,402

[22] Filed: May 13, 1980

[51] Int. Cl.³ .................. A61K 31/505; C07D 487/04
[52] U.S. Cl. ................................. 424/251; 424/273 R; 542/420; 542/417; 542/418
[58] Field of Search ................ 544/281, 279; 542/420; 548/302; 424/251, 273 R

[56] References Cited

U.S. PATENT DOCUMENTS

| | | | |
|---|---|---|---|
| 3,878,201 | 4/1975 | Tomcufcik | 424/251 |
| 4,152,436 | 5/1979 | Drabb, Jr. | 424/251 |
| 4,163,102 | 7/1979 | Lovell | 542/417 |

*Primary Examiner*—Mary C. Lee
*Assistant Examiner*—Sharon A. Gibson
*Attorney, Agent, or Firm*—Thomas J. Monahan

[57] ABSTRACT

There are provided certain oxalylated amidinohydrazones, and methods of use of the compounds for the control of insects, especially Lepidopterous insects, and for the control of ants, family Formicidae, especially fire ants.

26 Claims, No Drawings

OXALYLATED AMIDINOHYDRAZONES, METHOD FOR PREPARING SAME AND USE AS INSECT AND FIRE ANT CONTROL AGENTS

SUMMARY OF THE INVENTION

The present invention relates to novel insecticidal compounds of formula (I)

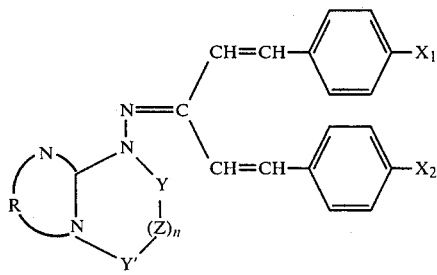

wherein R is $C_2$–$C_4$ alkylene chain which may optionally be substituted with one to four $C_1$–$C_3$ alkyl group(s) or with one phenyl group, —$CH_2$—$CH$=$CH$—$CH_2$—,

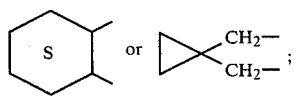

$X_1$ and $X_2$ each are halogen, $CF_3$, $CHF_2O$, $CF_3O$, $CHF_2CF_2O$, $CHF_2S$, $C_1$–$C_3$ alkyl, $C_1$–$C_3$ alkoxy, $C_1$–$C_3$ alkylthio, $C_1$–$C_3$ alkylsulfinyl or $C_1$–$C_3$ alkylsulfonyl; Y and Y' each are —$CH_2$— or

with the proviso that at least one of Y and Y' must be

Z is —$CH_2$—or —$C(CH_3)_2$—; n is 0 or 1, and when n is 1, both Y and Y' must be

A preferred group of compounds represented by formula (I) are those wherein $X_1$ and $X_2$ are as hereinabove defined; R is $C_2$–$C_4$ alkylene,

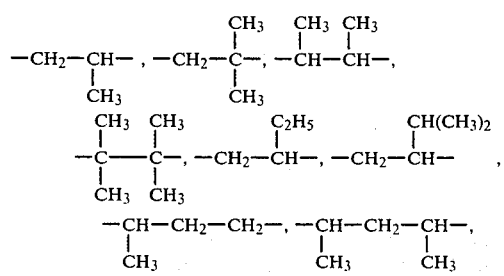

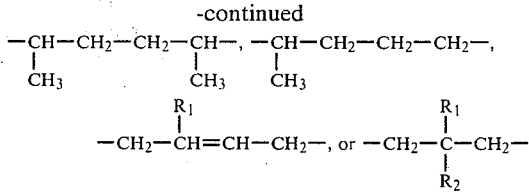

wherein $R_1$ and $R_2$ each are $C_1$–$C_3$ alkyl,

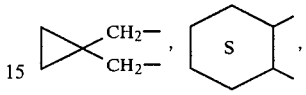

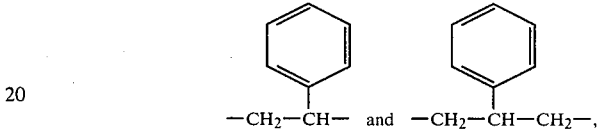

both Y and Y' are

and n is 0.

A more preferred group of compounds of formula (I) are those wherein both $X_1$ and $X_2$ are $CF_3$, $CF_3O$, Cl or Br; R is selected from

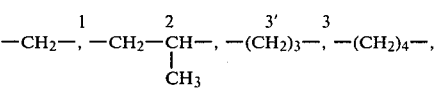

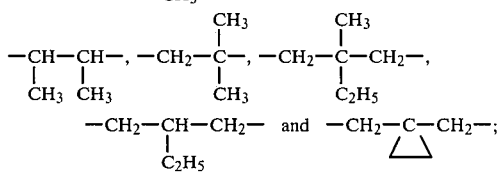

both Y and Y' are

and n is 0.

Another, equally preferred group of compounds represented by formula (I) are those wherein $X_1$ and $X_2$ each are selected from Cl, Br, I, $CF_3$, $CF_3O$, $CHF_2S$, $CHF_2CF_2O$, $C_2H_5$ or i—$C_3H_7$; R is

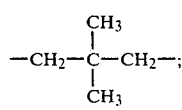

both Y and Y' are

and n is 0.

In general, the compounds of formula (I) can be conveniently prepared by reacting the corresponding pentadienone hydrazone of formula (II) wherein R, $X_1$ and $X_2$ are as hereinabove defined with a dicarboxylic acid chloride (or bromide) having the structure (III):

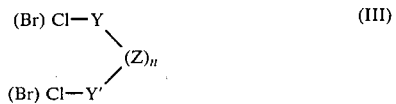

wherein Y and Y' both are

and Z and n are as hereinabove defined, or with an Ω halocarboxylic acid halide having the above (III) structure wherein only Y or Y' is

while the other must be —$CH_2$—; Z and n are as hereinabove defined in equimolar amounts in the presence of a base such as trialkylamine or an alkali metal carbonate or bicarbonate in the presence of an inert anhydrous solvent such as ether, as illustrated below using said formula (II) hydrazone and oxalyl chloride:

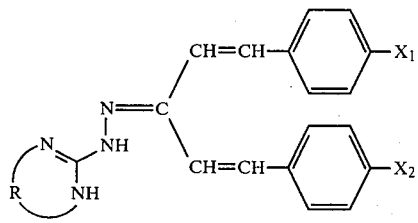

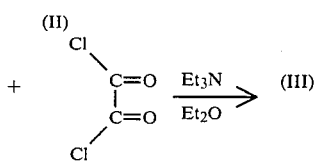

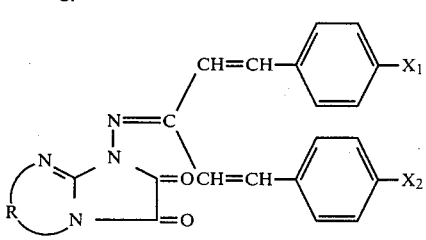

Alternatively, a compound of formula (II) may be reacted with an equimolar or excess amount of a dialkyl ester of a dicarboxylic acid at elevated temperatures and in the presence of an inert solvent, such as toluene, as shown below:

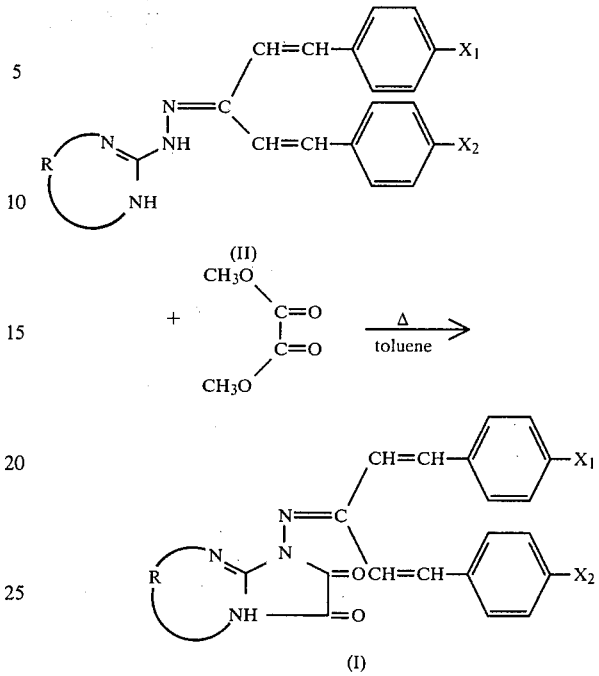

wherein in both of the reaction sequences shown above, R, $X_1$ and $X_2$ are as hereinbefore defined.

Thus for instance, the reaction of [3-[4-(trifluoromethyl)phenyl]-1-[2-(4-trifluoromethyl)phenyl]ethenyl]-2-propenylidene]tetrahydro-5,5-dimethyl-2(1H)-pyrimidinone hydrazone (IIa) with 1 to 3 molar equivalents and preferably 1 to 2 molar equivalents of oxalyl chloride in the presence of sufficient amounts of an acid acceptor such as a trialkylamine or an alkali metal carbonate or bicarbonate and an inert, anhydrous solvent such as ether affords the desired 1,5,6,7-tetrahydro-6,6-dimethyl-1-{{p-(trifluoromethyl)-2-(p-trifluoromethyl)-styryl]cinnamylidene}amino}imidazo[1,2-a]pyrimidine-2,3-dione (Ia) as shown below:

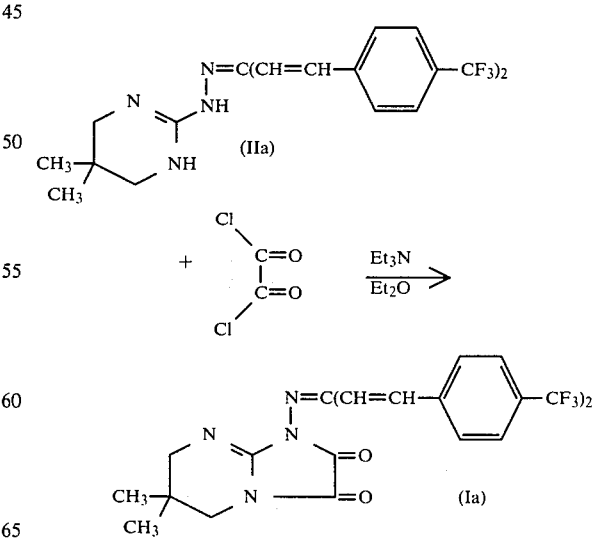

Similarly, when the compound of (IIa) is mixed with 1 to 3 molar equivalents, and preferably with 1 to 2 molar equivalents of a dialkyl oxalate, such as dimethyl oxalate and an inert solvent such as toluene, and the reaction mixture heated at an elevated temperature sufficiently high to distill out the alcohol formed in the reaction, formula (Ia) compound is obtained in satisfactory yields.

The intermediate hydrazones of formula (II) may be prepared by procedures similar to those disclosed in U.S. Pat. No. 4,152,436, issued May 1, 1979 and incorporated herein by way of reference.

Advantageously, the compounds of the invention find utility in controlling insects, particularly lepidopterous insects, and ants, family Formicidae, by contacting the insects with, and/or applying to their habitat or food supply, an insecticidally effective amount of a compound of formula (I)

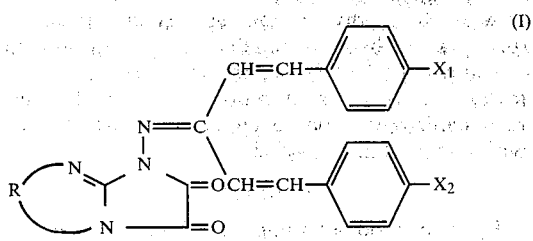

wherein R, $X_1$ and $X_2$ are as hereinabove defined. Further, the invention finds utility in protecting agronomic crops, trees, shrubs, ornamentals, and the like from attack by insects, by applying to the crops an insecticidally effective amount of a compound having the above-identified structure. In practice, from about 0.1 kg/hectare to 11.2 kg/hectare, and preferably 0.14 kg/hectare to 1.0 kg/hectare of a formula (I) compound is effective for insect control and/or for crop protection.

The desired compounds can be applied in either liquid or solid form. For instance, they may be applied in solid form as dusts or dust concentrates, or in liquid form as emulsifiable concentrates, flowable liquids or wettable powders which are dispersed in water or other inexpensive liquid for application as a finely divided spray.

A typical emulsifiable concentrate can be prepared by admixing from about 12% to 29% by weight of a formula (I) compound, about 8% to 12% by weight of a blend of nonionic emulsifiers, such as T-Mulz 339 (sold by Thompson-Hayward of Kansas City, Kansas) or polyoxyethylene derivatives and blends with alkyl aryl sulfonates, and about 59% to 80% by weight of cyclohexanone or a heavy aromatic solvent having a mixed aniline point between −1° C. and 35.0° C. (30° F. and 95° F.), a specific gravity between 0.880 and 1.5 at 15.5°/15.5° C. (60°/60° F.), and an aromatic content of 60% to 100%. These formulations provide from 119.8 g/liter to 239.6 g/liter of the active hydrazone, and are generally diluted with water for application as a dilute liquid. However, the formulations can also be applied in the form of undiluted discrete droplets as low volume or ultra-low volume sprays. For such application, the emulsifiable concentrate is usually applied with apparatus designed to disperse the liquid in the form of finely divided discrete droplets having a mass median diameter of from 25 to 150 microns.

A typical wettable powder formulation can be prepared by grinding together about 34% by weight of a synthetic calcium silicate, 12% by weight of a dispersing agent such as sodium lignosulfonate, 4% by weight of a wetting agent such as an alkyl aryl sulfonate, and 50% by weight of a compound of formula (I). Such formulation is generally dispersed in water for application as a liquid spray.

In general, the compounds of this invention are especially active and quite selective against Lepidopterous larvae such as southern armyworms [*Spodoptera eridania* (Cramer)], cabbage loopers [*Trichoplusia ni* (Hübner)], tobacco budworms [*Heliothis virescens* (Fabricius)], and the like, at 10 to 1000 ppm rates. They do not appear to be very toxic to most beneficial insects and thus are useful for pest management and integrated control programs, especially since they also show good residual insecticidal activity. Moreover, these compounds show virtually no phytotoxicity to plants at rates of application up to 11.2 kg/hectare.

Advantageously, the compounds of the present invention are active as stomach poisons. Thus, they are effective against insects with chewing mouth parts (Orthopterous insects such as cockroaches, grasshoppers, crickets and Isopterous insects, such as termites). They are effective for the control of fire ants, such as the southern fire ant, *Solenopsis xyloni*, the black imported fire ant, *Solenopsis richteri* and the red imported fire ant, *Solenopsis invicta*. They are also effective for the control of ants, such as the bigheaded ant, *Pheidole megacephala*, and the Argentine ant, *Iridomyrmax humilis*, that are dominant pests in pineapple and sugarcane fields, and for the control of many species of ants that are classified under the general category of household ants. Ants are serious economic and public health pests. Serious problems created by fire ants are stinging of humans and livestock, feeding on plants, particularly on seedlings and on germinating seeds, damage to farm machinery that strike ant mounds, loss of crops and refusal of workers to enter infested fields to cultivate and harvest crops. Ants invade houses, crawl over food, carry bits of food to their nests and also cause damage by establishing their nests in the woodwork of houses and other wooden buildings.

Control of these pests can be achieved with treated baits that are distributed in or adjacent to the infested area, such as pasture, park dwellings or other locations in which ant control is desired, and made available to worker ants. The workers carry the treated bait to the colony where it is consumed by the queens and the young ants, leading to their destruction.

In practice, generally about 1.25 g/ha to 75.0 g/na, and preferably 2.5 g/ha to 37.5 g/ha of a formula (I) compound is effective for fire ant control and/or for crop protection from ants and about 0.0625% to 4% by weight, and preferably 0.125% to 2.0% by weight of the compound is effective for the control of house ants and/or other insects that are controlled by bait.

Baits can be prepared, for example, by admixing these compounds with peanut butter or citrus pulp, vegetable oils such as soybean oil, animal fats such as lard and tallow, and with or without an organic filler such as bran, and/or an attractant such as lecithin. The composition is then placed in soda straws or on a carrier such as puffed grain, corncob grits and/or starch matrix and distributed in the area of the colony or infestation. Use of these baits has particular advantage, since such method of distribution poses little or no hazard to non-target organisms that may frequent the infested area.

The invention is further illustrated by the examples set forth below. These examples are provided only by way of illustration and are not intended to be limiting.

EXAMPLE 1

Preparation of
1,5,6,7-tetrahydro-6,6-dimethyl-1-{{p-(trifluoromethyl)-α-(p-trifluoromethyl)styryl]cinnamylidene}amino}imidazo[1,2-a]pyrimidine-2,3-dione Oxalyl chloride (2.5 g) is added slowly to a stirred mixture of [3-[4-(trifluoromethyl)phenyl]-1-[2-[4-(trifluoromethyl)phenyl]ethenyl]-2-propenylidene]tetrahydro-5,5-dimethyl-2-(1H)-pyrimidinone hydrazone (9.9 g), triethylamine (4.0 g) and dry ether (174 ml). After stirring the mixture for several hours, the solids are collected by filtration, washed with ether and then with water. A sample of the dried solids is recrystallized from a mixture of ethyl acetate and hexane to yield a yellow crystalline product, m.p. 225°–227° C. The infrared spectrum shows strong carbonyl absorption at 1700 and 1775 cm$^{-1}$. Analysis; calculated for $C_{27}H_{22}N_4O_2F_6$: C 59.12; H 4.04; N 10.22; Found: C 58.79; H 4.27; N 9.99.

EXAMPLE 2

Preparation of
1,5,6,7-tetrahydro-6,6-dimethyl-1-{{p-(trifluoromethyl)-α-(p-trifluoromethyl)styryl]cinnamylidene}amino}imidazo[1,2,-a]pyrimidine-2,3-dione Dimethyl oxalate (1.04 kg; 8.81 mol) and toluene (10 l) are mixed, and heated to reflux and ca 1.0 l toluene and residual water are collected by distillation. The mixture is then cooled and [3-[4-(trifluoromethyl)phenyl]-1-[2-[4-(trifluoromethyl) phenyl]ethenyl]-2-propenylidene]tetrahydro-5,5-dimethyl-2 (1H)-pyrimidinone hydrazone (2.0 kg; 4.04 mol) is added. The mixture is stirred and heated at reflux while about 4 l of toluene is removed at a reflux ratio of 5/1 to 6/1. The mixture is then allowed to cool slowly to room temperature, the precipitated solids are collected by filtration and washed successively with toluene (1 l) and with hexane (1 l) and dried at 50° C. There is obtained 1.93 kg (87% of theory) of pale yellow product; m.p. 210°–215° C. Recrystallization from about 8 l of acetonitrile yields 1.59 kg; m.p. 225°–227° C., relatively free of impurities as shown by thin layer chromatography on silica gel (toluene:dioxane:acetic acid=1:1:0.04). The proton magnetic resonance spectrum (DMSO-d6) showed the methyl protons as a singlet at about 1.0 (6H), the tetrahydropyrimidine ring protons as a multiplet at about 3.3 (4H), and the aromatic and vinyl proton(s) as a multiplet at about 7.3–8.2 (12H). Further recrystallization from acetonitrile afforded product with a m.p. of 233°–234° C.

EXAMPLE 3

By the method of Example 1 or Example 2 and substituting the appropriate acid hydrazone a number of compounds are made. These compounds are listed in Table I below.

TABLE I

| No. | R | X$_1$ | X$_2$ | m.p. °C. | Calculated C | Calculated H | Calculated N | Found C | Found H | Found N |
|---|---|---|---|---|---|---|---|---|---|---|
| 1 | —CH$_2$—CH$_2$— | CF$_3$ | CF$_3$ | 214–215 | 58.4 | 4.0 | 12.4 | 58.4 | 4.2 | 12.3 |
| 2 | —CH$_2$—CH(CH$_3$)— | CF$_3$ | CF$_3$ | 150–152 | 57.7 | 3.5 | 10.8 | 56.3 | 3.8 | 10.4 |
| 3 | —(CH$_2$)$_3$— | CF$_3$ | CF$_3$ | 251–252(d) | 57.7 | 3.5 | 10.8 | 57.5 | 3.8 | 10.7 |
| 4 | —(CH$_2$)$_4$— | CF$_3$ | CF$_3$ | 241–243 | 58.4 | 3.8 | 10.5 | 58.1 | 3.9 | 10.5 |
| 5 | —CH$_2$—CH(C$_6$H$_5$)— | CF$_3$ | CF$_3$ | 108–112 | 61.9 | 3.5 | 9.6 | 59.0 | 4.4 | 8.6 |
| 6 | —CH$_2$—C(CH$_3$)$_2$— | CF$_3$ | CF$_3$ | 165–169 | 58.4 | 3.8 | 10.5 | 57.7 | 4.3 | 10.4 |
| 7 | —CH$_2$—C(CH$_3$)(C$_2$H$_5$)—CH$_2$— | CF$_3$ | CF$_3$ | 216–218(dec.) | 59.8 | 4.3 | 10.0 | 59.5 | 4.3 | 9.8 |
| 8 | —CH$_2$—C(cyclopropyl)—CH$_2$— | CF$_3$ | CF$_3$ | 229–231 | 59.3 | 3.7 | 10.3 | 59.7 | 3.8 | 10.2 |
| 9 | —CH$_2$—C(cyclopropyl)—CH$_2$— | OCF$_3$ | OCF$_3$ | 225–226 | 56.1 | 3.5 | 9.7 | 55.9 | 3.5 | 9.8 |
| 10 | —CH$_2$—C(cyclopropyl)—CH$_2$ | Br | Br | 236–238 | 52.8 | 3.5 | 9.9 | 52.7 | 3.7 | 9.9 |

TABLE I-continued

[Structure: An imidazo-pyrimidine system with R group, connected through N-N=C with two CH=CH-phenyl-X substituents]

| No. | R | X$_1$ | X$_2$ | m.p. °C. | Calculated C | H | N | Found C | H | N |
|---|---|---|---|---|---|---|---|---|---|---|
| 11 | —CH$_2$—C—CH$_2$ (cyclopropyl) | OCHF$_2$ | OCHF$_2$ | 192–196 | 59.8 | 4.1 | 10.3 | 60.6 | 4.3 | 9.7 |
| 12 | —CH$_2$CH=CH—CH$_2$ | CF$_3$ | CF$_3$ | 207–208 | 58.7 | 3.4 | 10.5 | 58.9 | 3.9 | 10.2 |

EXAMPLE 4

By the method of Example 1 or Example 2 a number of compounds are made. These compounds are listed in Table II below:

TABLE II

[Structure: 6,6-dimethyl-tetrahydro imidazo-pyrimidine system with N-N=C linked to two CH=CH-phenyl-X substituents]

| No. | X$_1$ | X$_2$ | m.p. °C. | Calculated C | H | N | Found C | H | N |
|---|---|---|---|---|---|---|---|---|---|
| 1 | Cl | Cl | 242–244(d) | 62.4 | 4.6 | 11.6 | 62.3 | 4.7 | 11.6 |
| 2 | Br | Br | 218–220 | 52.7 | 3.9 | 9.8 | 53.5 | 4.1 | 9.2 |
| 3 | CF$_3$ | Cl | 225–227 | 60.6 | 4.3 | 10.9 | 61.0 | 4.4 | 10.9 |
| 4 | CF$_3$O | CF$_3$O | 225–226 | 55.9 | 3.8 | 9.6 | 56.1 | 4.1 | 9.7 |
| 5 | CHF$_2$S | CHF$_2$S | 158–160 | 56.2 | 4.2 | 9.7 | 56.5 | 4.2 | 9.6 |
| 6 | i-C$_3$H$_7$ | i-C$_3$H$_7$ | 207–211 | 75.0 | 7.3 | 11.3 | 75.0 | 7.3 | 11.2 |
| 7 | I | I | 249–251 | 45.2 | 3.3 | 8.4 | 45.3 | 3.3 | 8.4 |
| 8 | C$_2$H$_5$ | C$_2$H$_5$ | 192–194 | 74.3 | 6.9 | 12.0 | 74.1 | 6.9 | 11.8 |
| 9 | C$_2$H$_5$O | C$_2$H$_5$O | | | | | | | |
| 10 | CHF$_2$CF$_2$O | CHF$_2$CF$_2$O | 184–187 | 54.0 | 3.8 | 8.7 | 55.4 | 4.2 | 8.2 |
| 11 | CF$_3$ | C$_2$H$_5$O | 241–243(dec) | 64.5 | 5.2 | 10.7 | 63.5 | 5.1 | 10.4 |
| 12 | CHF$_2$O | CHF$_2$O | 196–198 | 59.6 | 4.4 | 10.3 | 59.6 | 4.5 | 10.3 |
| 13 | Cl | n-C$_3$H$_7$O | 219–221.5 | 66.6 | 5.8 | 11.1 | 66.0 | 5.8 | 11.2 |
| 14 | Br | Cl | 232.235 | 57.1 | 4.2 | 10.7 | 57.0 | 4.3 | 10.3 |

EXAMPLE 5

Preparation of Imidazo[1,2-a]pyrimidin-3(2H)-one, 1,5,6,7-tetrahydro-1-{{p-(trifluoromethyl)-α-[p-(trifluoromethyl)styryl]cinnamylidene}amino}

A sample of 1,4-pentadiene-3-one, 1,5-bis(α,α,α-trifluoro-p-tolyl)-, 1,4,5,6-tetrahydro-2-pyrimidinylhydrazone (2.3 g, 0.005 mole) was added to 50 ml of toluene at 40°–45° followed by chloroacetic anhydride (0.9 g, 0.005 mole). The resulting solution was allowed to cool and stand at room temperature for several days. The mixture was then filtered to remove 1.5 g (59%) of pale yellow solid. The product was purified by slurrying 1.3 g with 13 mol of ethyl acetate and filtering to get 1.1 g. In this way, the starting material was removed. The product was then partitioned between ethyl acetate and 10% potassium carbonate solution. The ethyl acetate layer was separated and dried over magnesium sulfate. Removal of the drying agent by filtration and concentration of the filtrate in vacuo left 0.8 g (32%) of a pale yellow solid m.p. 158°–160° C. Analysis: Calculated for C$_{25}$H$_{20}$N$_4$OF$_6$: C, 59.28; H, 3.95; N, 11.07. Found: C, 58.79; H, 4.01; N, 11.00.

EXAMPLE 6

Preparation of Imidazo[1,2-a]pyrimidin-3(2H)-one, 1,5,6,7-tetrahydro-6,6-dimethyl-1-{{p-(trifluoromethyl)-α-[p-trifluoromethyl)styryl]cinnamylidene}amino}

The preparation of the title compound was carried out in a manner analogous to the preparation of Example 5 starting with [3-[4-(trifluoromethyl)phenyl]-1-[2[4-(trifluoromethyl)phenyl]ethenyl]-2-propenylidene]tetrahydro-5,5-dimethyl-2(1H)-pyrimidone hydrazone. A yellow solid was isolated with m.p. 150°–157°. The analytical sample, recrystallized from acetonitrile, has m.p. 152°–157°. Analysis: Calculated for C$_{27}$H$_{24}$F$_6$N$_4$O: C, 60.67; H, 4.49; N, 10.48. Found: C, 60.44; H, 4.64; N, 10.36.

EXAMPLE 7

Preparation of
2H-Pyrimido[1,2-a]Pyrimidine-2,4-(3H)-dione,
1,6,7,8-tetrahydro-3,3-dimethyl-1-{{p-(trifluoromethyl)-α-[p-(trifluoromethyl)styryl]cinnamylidene}amino}

A solution of α,α-dimethylmalonic acid (0.65 g, 0.0049 mole) and thionyl chloride (0.77 ml, 0.0104 mole) in 5 ml of benzene containing one drop of dimethylformamide was stirred 2 hours at reflux. The resulting mixture was cooled then added dropwise, under a nitrogen atmosphere, to a suspension of 1,4-pentadiene-3-one, 1,5-bis(α,α,α-trifluoro-p-tolyl),-1,4,5,6-tetrahydro-2-pyrimidinylhydrozone (2.2 g, 0.0047 mole) and quinuclidine (1.05 g, 0.0094 mole) in 5 ml of benzene at 10° C. The reaction was stirred overnight slowly warming to room temperature. The mustard-colored solids were filtered off and washed with 50 ml each of ether and H$_2$O. The insoluble light beige powder which remained at the interface was collected to give 1.1 g (42%) of product; m.p. 214°–218° C., Analysis: Calculated for C$_{28}$H$_{24}$F$_6$N$_4$O$_2$: C, 59.78; H, 4.30; N, 9.96. Found: C, 58.93; H, 4.27; N, 9.83.

EXAMPLE 8

Preparation of
2H-Pyrimido[1,2-a]pyrimidine-2,4-(3H)-dione,
1,6,7,8-tetrahydro-3,3,7,7-tetramethyl-1-{{p-trifluoromethyl)-α-[p-(trifluoromethyl)styryl]cinnamylidene}amino}

Following the procedure of Example 7, using [3-[4-(trifluoromethyl)phenyl]-1-[2-[-(trifluoromethyl)-phenyl]ethenyl]-2-propenylidene]tetrahydro-5,5-dimethyl-2(1H)-pyrimidinone hydrazone, the product was obtained as a yellow solid, m.p. 133°–134° (resolidified and melts at 194°). Analysis: Calculated for C$_{30}$H$_{28}$F$_6$N$_4$O$_2$: C, 61.0; H, 418; N, 9.5. Found: C, 60.9; H, 4.9; N, 9.5.

EXAMPLE 9

Evaluation of the Insecticidal Activity of the Compound of the Invention

Methods

1. Tobacco budworm (*Heliothis virescens*), 1st instar.

Formulations

The compounds to be tested are dissolved in 50:50 acetone:water to yield solutions of 300,100 and 10 ppm concentration, respectively.

Plant Preparation

Cotton plants with the first true leaf expanded about 6–7 cm in length are selected for the test.

Insect Preparation

Cheesecloth on which moths have oviposited is daily cut into 10–20 mm squares containing 50–100 eggs each. These squares are held at 21° C. for two days and at 24° C. for another day in order to coordinate hatch with testing times. Thus, the worms are 0–2 hours old at the time of use.

Test Procedure

The cotton plant is dipped in the test formulation, agitated for 3 seconds, and placed in a hood to dry. When dry, the leaf is removed from the plant and placed in an "8-ounce Dixie cup #2168 ST" (240 ml, 6 cm high, top diameter 9.5 cm, bottom diameter 8 cm) to which a 5 cm length of damp cotton dental wick had been previously added. A square of cheesecloth with newly hatched budworm larvae on it is placed on the treated leaf, a clear plastic lid (Dixie #3068 G) is put on the cup, and the cups are held at 27° C. for two days. After two days mortality counts are made. Observation of the amount of feeding is also recorded. Where there is only trace to light feeding, the cup is held an extra day and results recorded at that time.

2. Southern armyworm (*Spodoptera eridania*), 3rd instar.

Formulations

The compounds to be tested are dissolved in 2:1 acetone:water to yield solutions of 1000, 100 and 10 ppm concentration, respectively.

Plant Preparations

Sieva lima bean plants are selected with primary leaves 7–8 cm long and cut back to one plant per pot.

Insect Preparation

The bottom of a 100×10 mm petri dish is lined with a damp filter paper and ten 3rd instar larvae, each about 10 mm long, are added.

Test Procedure

The bean plant is dipped in the test solution, agitated for 3 seconds and placed in a hood to dry. When dry, one leaf is removed from the plant and placed in the petri dish with the caterpillars. The dish is held at 27° C. The plant with the remaining leaf is held in the greenhouse under high intensity lights.

Mortality counts are made after two days. If any reduction in feeding is noted, the dish is held for an additional day and reobserved. Mortality counts and reduced feeding are again determined, and the bean plants treated with compounds considered active are retained in the greenhouse exposed to high intensity lights for a 7-day residual activity test. One week after the original treatment, a leaf is removed from the plant and assayed again by the above procedure. The results yield a measure of the residual activity of the compound under test.

3. Mexican bean beetle (*Epilachna varivestis*), larva.

Formulations

The compounds to be tested are dissolved in 50:50 acetone:water to yield solutions of 300,100 and 10 ppm concentration, respectively.

Plant Preparation

Sieva lima bean plants are selected with primary leaves 7–8 cm long, and cut back to one plant per pot.

Insect Preparation

The bottom of a 100×10 mm petri dish is lined with a damp filter paper and ten last instar larvae, about 13 days old, are put in the dish.

Test Procedure

The bean plant is dipped in the test solution, agitated for 3 seconds and placed in a hood to dry. When dry, one leaf is removed and placed in the petri dish with the insects. The 2nd leaf is added the next day. The dish and the remaining plant are held at 27° C.

Two days after treatment mortality counts are made. The test is retained until the adult beetles emerge and then reevaluated. At this time, about 9–10 days post-treatment, the dish is examined for dead larvae, dead pupae or adults, deformed pupae or adults, larvae-pupal intermediates or pupal-adult intermediates, or any other interference with normal molting, transformation and emergence of pupae or adults.

4. Cotton boll weevil (*Anthonomus grandis*), adult.

Test Formulations

The compounds to be tested are dissolved in 2:1 acetone:water to yield solutions of 1000 and 100 ppm concentration.

Insect Preparation

The bottom of a 100×10 mm petri dish is lined with a damp filter paper and ten adult boll weevils are added to the dish.

Test Procedure

A cotton cotyledon is dipped in the test solution, agitated for 3 seconds and placed in a hood to dry. When dry, it is put in the petri dish with the insects. The dishes are held at 27° C. for two days.

Mortality counts are made, prodding each insect with a dull pencil point to distinguish dead ones from those "playing dead".

5. Tobacco budworm (*Heliothis virescens*), 3rd instar.

Formulations

The compounds to be tested are dissolved in 2:1 acetone:water to yield solutions of 1000, 100 and 10 ppm concentration, respectively.

Test Procedure

Cotton cotyledons are dipped in the solutions and dried in a hood. When dry, each cotyledon is cut into quarters, and ten sections are placed individually in 30 ml plastic medicine cups containing a 5–7 mm long piece of damp cotton dental wick. One 3rd instar budworm larvae is added to each cup and a cardboard lid placed on the cup. The cups are held at 27° C. for 3 days. Mortality counts and observations of reduced feeding are then made.

6. Cabbage looper (*Trichoplusia ni*), 3rd instar.

Formulations

The compounds to be tested are dissolved in 2:1 acetone:water to yield solutions of 1000, 100 and 10 ppm concentration, respectively.

Plant Preparation

Cotton plants with the first time leaf expanded about 7–8 cm in length are selected for the test.

Insect Preparation

The bottom of a 100×10 mm petri dish is lined with a damp filter paper and ten 3rd instar larvae are added.

Test Procedure

The cotton plant is dipped in the test solution, agitated for 3 seconds and placed in a hood to dry. When dry, the leaf is placed on the petri dish with the insects. The dish is held at 27° C. for one or two days, and then mortality counts and observations of reduced feeding are made.

7. German Cockroach (*Blattella germanica*), bait test.

Formulations

Cornmeal baits of 1000 ppm and 100 ppm are prepared by pipetting 1 ml of the appropriate concentration of a solution of test compound onto 1 g of cornmeal in a 30 ml wide-mouth bottle. A gentle stream of air is passed into the bottom until the baits are dry.

Test Procedure

To 1-pint wide-mouth Mason jars (about 500 ml), each containing 1 g of bait prepared as above, are added ten adult male cockroaches (per jar) and a screen lid placed on the jars. After one day a small wad of cotton soaked in 10% honey solution is placed on the top of each screen lid. During the test the jars are held at 27° C.

One day posttreatment initial knockdown or kill is determined. Final observations are made 4 days post-reatment.

8. German Cockroach (*Blattella germanica*) residue test.

Formulations

The compounds to be tested are dissolved in acetone to yield solutions of 1000 and 100 ppm concentration.

Test Procedures

150×15 mm Petri dishes are used. 1 ml of the test solution is pipetted slowly over the bottom of the dish so as to give as uniform coverage as possible. This yields a deposit of about 1 mg/150 cm$^2$ when using 1000 ppm test solutions. The dishes are allowed to dry on the open bench top, following which 10 adult male cockroaches are placed in each dish and the cover put on the petri dish, and the dishes are then held at 27° C.

Treatments are observed at one day posttreatment for initial knockdown or kill. Final observations are made 4 days posttreatment.

The data obtained by the above tests are summarized in Tables III and IV, wherein it can be seen, that the compounds of the invention effectively control insects, especially lepidopterous insects.

TABLE III

Evaluation of the insecticidal activity of the compounds of the invention represented by formula:

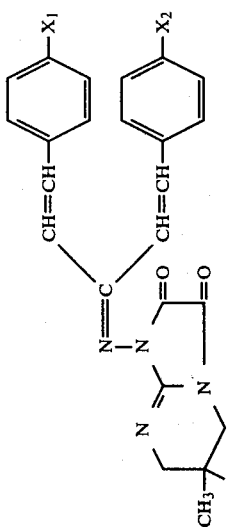

Percent[1] mortality counts are given at the parts per million (ppm) concentrations shown

| Compound | | Tobacco budworm 1st instar -ppm- | | | Southern armyworm 3rd instar -ppm- | | | 7* days | Mexican bean beetle larva -ppm- | | | Boll weevil adult -ppm- | | | Tobacco budworm 3rd instar -ppm- | | | Cabbage looper 3rd instar -ppm- | | | German cockroach adult male | | | | |
|---|---|---|---|---|---|---|---|---|---|---|---|---|---|---|---|---|---|---|---|---|---|---|---|---|---|
| | | | | | | | | | | | | | | | | | | | | | Bait -ppm- | | | Residual -ppm- | |
| $X_1$ | $X_2$ | 300 | 100 | 10 | 1000 | 100 | 10 | | 300 | 100 | 10 | 1000 | 100 | 10 | 1000 | 100 | 10 | 1000 | 100 | 10 | 1000 | 100 | 1000 | 100 |
| Cl | Cl | 100 | 100 | 0 | 100 | 100 | 50 | 100 | 100 | 100 | 0 | 100 | 0 | 0 | 100 | 80 | 0 | 100 | 100 | 20 | 100 | 0 | 0 | |
| | | | | | | | | 80 | 90 | 90R | | 90 | | | | | | | | | | | | |
| Br | Br | 100 | 100 | 0 | 100 | 100 | 100 | 0 | 70 | | | 40 | | | 90 | | 60 | 100 | | 60 | 100 | 80 | 0 | 0 |
| | | | | | | | 100 | 0 | | | | | | | 60 | | 100 | | | | | | | |
| | | | | | | | 100 | 0 | | | | | | | | | | | | | | | | |
| CF$_3$ | Cl | 100 | 100 | 0 | 100 | 100 | 100 | 100 | 100 | 100 | 0 | 0 | 0 | | 100 | 100 | 30 | 100 | 100 | 80 | 20 | 0 | 0 | |
| | | | | | | | | 0 | | | | | | | 90 | | 100 | | | | | | | |
| CF$_3$O | CF$_3$O | 0 | | | 100 | 100 | 0 | 0 | 70 | | | 40 | | | 100 | 60 | 0 | 100 | 100 | 0 | 90 | 0 | 0 | |
| CHF$_2$S | CHF$_2$S | 100 | 0 | | 100 | 100 | 0 | 0 | 90 | 0 | | 0 | | | 100 | | 0 | 100 | 100 | 0 | 0 | 0 | 0 | |
| i-C$_3$H$_7$ | i-C$_3$H$_7$ | 100 | 100 | 0 | 100 | 100 | 0 | 100 | 0 | | | 60 | | | 100 | 50 | 0 | 100 | 100 | 100 | 0 | | 0 | |
| | | | | | | | 100 | 0 | | | | | | | | | | 100 | | | | | | |
| CF$_3$ | CF$_3$ | 100 | 100 | 0 | 100 | 100 | 90 | 0 | 50 | | | 40 | 0 | 0 | 100 | 100 | 20 | 100 | 100 | 90 | 100 | 70 | 0 | 0 |
| | | | | | | 100 | 0 | 0 | 60 | | | 50 | 0 | 0 | 100 | 100 | 0 | 100 | 90 | 0 | 30 | 0 | 0 | |
| I | *** | 100 | 70 | | 100 | 100 | 0 | 60 | 0 | 0 | | 50 | 0 | 0 | 100 | 0 | | 100 | 90 | 100 | 20 | 0 | 0 | |
| F$_2$CH—CF$_2$O | F$_2$CHO | 0 | 0 | 0 | 100 | 30 | 90 | 0 | 0 | 0 | 0 | 0 | 0 | 0 | OR** | OR | | 90R | 40R | 100 | 50 | 0 | 0 | 0 |
| F$_2$CHO | C$_2$H$_5$O | | | | 100 | 100 | 0 | | 80 | 0 | 0 | 0 | 0 | 0 | 100 | 90 | | | | | | | | |
| CF$_3$ | n-C$_3$H$_7$O | 100 | 100 | 0 | 100 | 100 | 0 | | 30 | 0 | | 0 | | | 100 | 40 | 20 | 100 | 100 | 20 | 0 | 40 | 0 | 0 |
| Cl | Cl | 100 | 80 | 0 | 100 | 100 | 70 | | 0 | | | 0 | | | 80 | | | — | | | 100 | | | |
| Br | | | | | | | | | | | | | | | | | | | | | | | | |

\* = 7-day residual test  
** R = repellent  
*** = F$_2$CH—CF$_2$O substituted on $X_1$ and $X_2$  
(1) = a range is shown where more than 10 insects are used for the test

TABLE IV

Evaluation of the insecticidal activity of the compounds of the invention represented by formula:

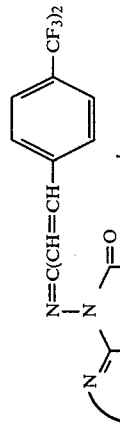

Percent[1] mortality counts are given at the parts per million (ppm) concentrations shown

| R | Tobacco budworm 1st instar -ppm- | | | Southern armyworm 3rd instar -ppm- | | | | Mexican bean beetle larva -ppm- | | | Boll weevil adult -ppm- | | Tobacco budworm 3rd instar -ppm- | | | Cabbage looper 3rd instar -ppm- | | | German cockroach adult male Bait -ppm- | | Residual -ppm- | |
|---|---|---|---|---|---|---|---|---|---|---|---|---|---|---|---|---|---|---|---|---|---|---|
| | 300 | 100 | 10 | 1000 | 100 | 10 | 7* days | 300 | 100 | 10 | 1000 | 100 | 1000 | 100 | 10 | 1000 | 100 | 10 | 1000 | 100 | 1000 | 100 |
| —CH₂—CH₂— | 65-75 | 0 | | 100 | 100 | 20 | 0 | 0 | | | 0 | | 100 | 60 | 0 | 100 | 100 | 0 | 30 | 0 | 0 | 100 |
| —CH₂—CH— \| CH₃ | 100 | 100 | 0 | 100 | 100 | 100 | 0 | 0 | | | 90 | 0 | 100 | 80 | 0 | 100 | 100 | 0 | 100 | 0 | 100 | |
| —(CH₂)₃— | 100 | 100 | 0 | 100 | 100 | 50 | 100 40 | ** 100 R | ** 90 R | 0 | 70 | | 100 | 80 | 0 | 100 | 100 | 0 | 100 | 0 | 0 | |
| —(CH₂)₄— | 100 | 75-85 | 0 | 100 | 100 | 30 | — 0 0 | 50 30 | | | — | | 100 | 90 | 0 | 100 | 100 | 30 | 20 | 0 | 0 | |
| CH₃ \| —CH₂—C— \| CH₃ | 100 | 100 | 0 | 100 | 100 | 60 | | 0 | 0 | 0 | 0 | | 100 | 90 | 0 | 100 | 100 | 80 | 100 | 40 | 0 | |
| —CH₂—C—CH₂— △ | 100 | 100 100 | 25-35 85-95 | 100 | 100 100 | 100 100 | 50 20 | 100 | 100 | 0 | 80 | 70 | 100 | 100 | 90 20 | 100 | 100 | 90 100 | 90 | 0 | 40 | 0 |
| —CH₂—C—CH₂— △ + | 100 | 100 | 0 | 100 | 100 | 100 | 100 | 0 | 0 | 0 | 0 | | 100 | 100 | 40 | 100 | 100 | 30 | 20 | 0 | 0 | 0 |
| —CH₂—C—CH₂— △ ++ | 100 | 40 | 0 | 100 | 100 | 80 | 30 | 50 | 0 | 0 | 80 | 0 | 100 | 80 | 0 | 100 | 100 | 80 | 30 | 0 | 0 | 0 |
| —CH₂—C—CH₂— △ +++ | 0 | 0 | 0 | 100 | 90 | 0 | | 0 | 0 | 0 | 0 | 0 | 30 | 0 | 0 | 60 | 0 | 0 | 0 | 0 | 0 | 0 |
| —CH₂—CH— ⌬ | 90 | 60 | 0 | 100 | 100 | 100 | | 0 | 0 | 0 | — | | 90 | | | 100 | 80 | | 0 | | 0 | 0 |

TABLE IV-continued

Evaluation of the insecticidal activity of the compounds of the invention represented by formula:

Percent[1] mortality counts are given at the parts per million (ppm) concentrations shown

| R | Tobacco budworm 1st instar -ppm- | | | Southern armyworm 3rd instar -ppm- | | 7* days | Mexican bean beetle larva -ppm- | | Boll weevil adult -ppm- | | Tobacco budworm 3rd instar -ppm- | | Cabbage looper 3rd instar -ppm- | | German cockroach adult male | | |
|---|---|---|---|---|---|---|---|---|---|---|---|---|---|---|---|---|---|
| | 300 | 100 | 10 | 1000 | 100 | | 300 | 10 | 1000 | 100 | 1000 | 100 | 1000 | 100 | Bait -ppm- | | Residual -ppm- |
| | | | | | | | | | | | | | | | 1000 | 100 | 1000 | 100 |
| 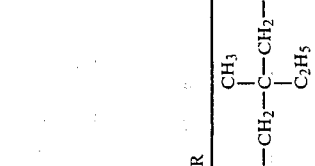 | 100 | | | 100 | 100 | | 100 | 0 | | 100 | | | | | | 10 | | 100 |

\* = 7 day residual test
\*\* = R = repellent
+ = In this compound the CF$_3$ groups have been replaced by CF$_3$O groups
(1) = A range is shown more than 10 insects are used for the test.
+ + = In this compound the CF$_3$ groups have been replaced by Br.
+ + + = In this compound the CF$_3$ groups have been replaced by F$_2$CHO groups.

EXAMPLE 10

Evaluation of the Residual Insecticidal Activity of the Compounds of the Invention By the following method, the residual insecticidal activity of the oxalylated amidinohydrazones of the present invention are compared with their respective precursors.

Method

Insect: Tobacco budworm (*Heliothis virescens*), 3rd instar.

Formulations: The compounds to be tested are dissolved in 50:50 acetone: water to yield solutions of 1000, 500 and 100 ppm concentrations, respectively.

Plant preparation: Cotton plants (variety Stoneville 213) are grown in the greenhouse in plastic pots 10 cm in diameter and thinned to one plant per pot. When plants have 2 true leaves expanded, they are ready for treatment.

Test procedure: The cotton plants are sprayed individually on a turntable that is rotating at 4 rpm. Plants are sprayed for 3 full revolutions using a #154 DeVilbiss atomizer operated at 0.15 kg/cm$^2$ pressure. The spray tip is held about 15 cm from the plant and the spray directed so as to give complete coverage of the plant. The plants are air-dried in the laboratory before being sampled or held for periodic bioassays. Plants are bioassayed at 0 days and after 1 day in the greenhouse under high intensity discharge lamps. The lights are operated for 14 hours a day. While held in the greenhouse, care is taken to avoid getting the foliage wet when the plants are watered.

Sampling: Treated true leaves are removed from the plants and placed in 10 cm diameter petri dishes prepared with a damp filter paper in the bottom, and then 5 third-instar tobacco budworm larvae are added to each dish. Dishes are held at 27°C. for 4–6 days.

Mortality counts are made and the amount of feeding damage is determined 4–6 days after the initial infestation.

The data obtained are summarized in Table V below, wherein it can be clearly seen that the oxalylated amidinohydrazones of the present invention have better residual insecticidal activity than their respective precursors.

TABLE V

A Comparison of Initial and Residual Insecticidal Activity for Oxalylated Versus Non-oxalylated Amidinohydrazones
Percent Mortality of Third-Instar Tobacco Budworm Larvae (*Heliothis virescens*)

| Compound | Conc. (ppm) | Day Sampled 0* | 1** |
|---|---|---|---|
| (7-membered diazepine)-NH-N=C(-CH=CH-C6H4-CF3)2 | 100 | 100 | 55 |
| (7-membered diazepine, oxalylated)-N-N=C(-CH=CH-C6H4-CF3)2 | 100 | 65 | 90 |
| H3C,H3C-(diazine)-NH-N=C(-CH=CH-C6H4-CF3)2 | 100 | 100 | 65 |
| H3C,H3C-(diazine, oxalylated)-N-N=C(-CH=CH-C6H4-CF3)2 | 100 | 100 | 100 |
| H3C,H3C-(diazine)-NH-N=C(-CH=CH-C6H4-Cl)2 | 100 | 11 | 35 |
| H3C,H3C-(diazine, oxalylated)-N-N=C(-CH=CH-C6H4-Cl)2 | 100 | 20 | 50 |
| H3C,H3C-(diazine)-NH-N=C(CH=CH-C6H4-Br)2 | 100 | 60 | 35 |
| H3C,H3C-(diazine, oxalylated)-N-N=C(CH=CH-C6H4-Br)2 | 100 | 10 | 45 |
| H3C,H3C-(diazine)-NH-N=C(CH=CH-C6H4-CH(CH3)2)2 | 1000 | 100 | 40 |

TABLE V-continued
A Comparison of Initial and Residual Insecticidal Activity for Oxalylated Versus Non-oxalylated Amidinohydrazones
Percent Mortality of Third-Instar Tobacco Budworm Larvae (*Heliothis virescens*)
| Compound | Conc. (ppm) | Day Sampled 0* | 1** |
|---|---|---|---|
| 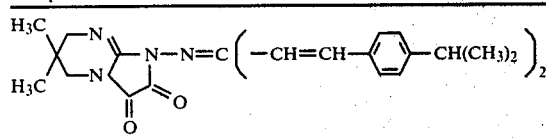 | 1000 | 100 | 100 |
| 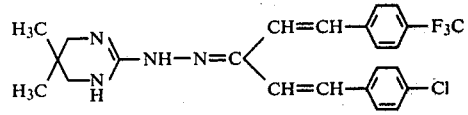 | 100 | 55 | 50 |
| 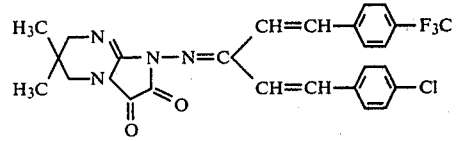 | 100 | 40 | 75 |
| 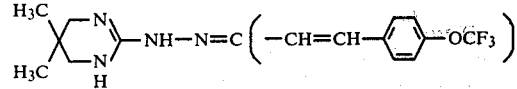 | 100 | 90 | 45 |
| 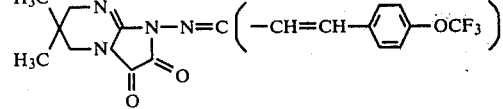 | 100 | 95 | 75 |
| 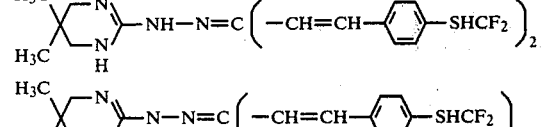 | 500 | 80 | 50 |
| 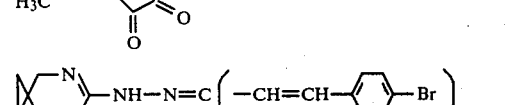 | 500 | 100 | 70 |
|  | 100 | 40 | 40 |
| 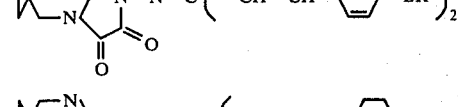 | 100 | 80 | 55 |
| 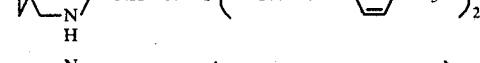 | 100 | 100 | 50 |
| 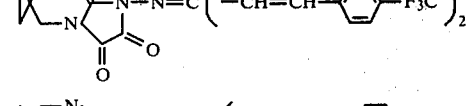 | 100 | 100 | 90 |
| 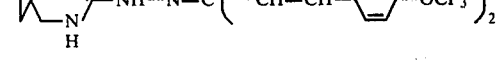 | 100 | 100 | 25 |
| 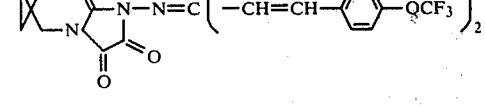 | 100 | 100 | 85 |
| 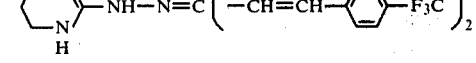 | 100 | 30 | 70 |

TABLE V-continued

A Comparison of Initial and Residual Insecticidal Activity for Oxalylated Versus Non-oxalylated Amidinohydrazones
Percent Mortality of Third-Instar Tobacco Budworm Larvae (*Heliothis virescens*)

| Compound | Conc. (ppm) | Day Sampled 0* | 1** |
|---|---|---|---|
| 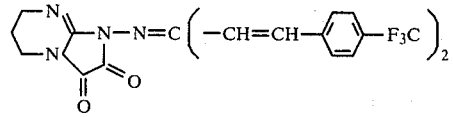 | 100 | 15 | 60 |
| 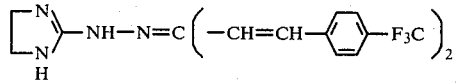 | 100 | 41 | 15 |
| 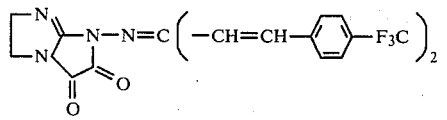 | 100 | 20 | 70 |
| 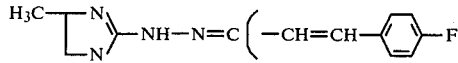 | 100 | 29 | 60 |
| 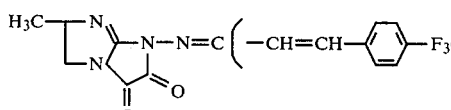 | 100 | 41 | 60 |
| 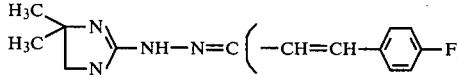 | 100 | 100 | 50 |
| 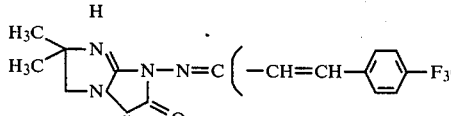 | 100 | 68 | 35 |

*Mortality readings made 4 days after treated leaves were sampled for assay.
**Mortality readings made 6 days after treated leaves were sampled for assay.

We claim:
1. A compound having the structure:

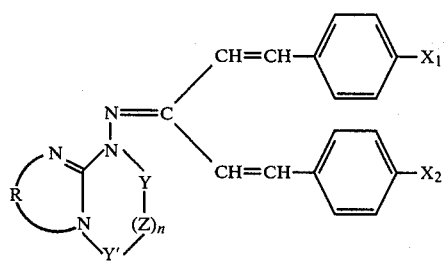

wherein R is a $C_2$–$C_4$ alkylene chain which may be substituted with one or two $C_1$–$C_2$ alkyl group(s) or with one phenyl group; or —CH$_2$—CH=CH—CH$_2$—; $X_1$ and $X_2$ each is halogen, CF$_3$, CHF$_2$O, CF$_3$O, CHF$_2$CF$_2$O, CHF$_2$S, $C_1$–$C_2$ alkyl or $C_1$–$C_3$ alkoxy; Y and Y′ each is —CH$_2$— or

but at least one substituent must be

Z is —CH$_2$— or —C(CH$_3$)$_2$—; n is 0 or 1; and when n is 1, Y and Y′ must be

2. A compound according to claim 1, wherein $X_1$ and $X_2$ each are bromine, chlorine, iodine, CF$_3$, CF$_3$O, CHF$_2$S, CHF$_2$CF$_2$O or $C_2$H$_5$; R is —CH$_2$—CH$_2$—, —CH$_2$—CH—, —(CH$_2$)$_3$—,
                          |
                          CH$_3$ —(CH$_2$)$_4$—, —CH—CH—, —CH$_2$—C—,
              |    |              |
              CH$_3$ CH$_3$        CH$_3$
                                   |
                                   CH$_3$ CH$_3$              CH$_3$
         |                  |
—CH$_2$—C—CH$_2$—, —CH$_2$—C—CH$_2$—or—CH$_2$—CH—CH$_2$—;
         |                  |              |
         CH$_3$              C$_2$H$_5$      C$_2$H$_5$ both Y and Y′ are

and n is 0.

3. A compound according to claim 1, wherein $X_1$ and $X_2$ are both Cl, Br, $CF_3$ or $CF_3O$; R is

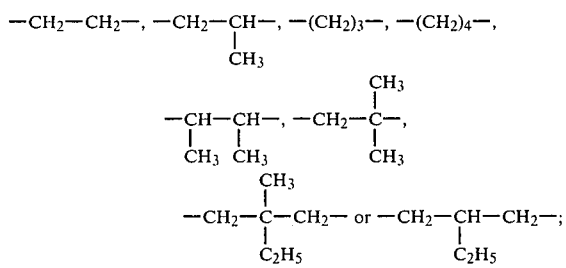

both Y and Y' are

and n is 0.

4. A compound according to claim 1, wherein $X_1$ and $X_2$ are bromine, chlorine, iodine, $CF_3$, $CF_3O$, $CHF_2S$, $CHF_2CF_2O$ or $C_2H_5$; R is

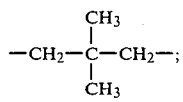

both Y and Y' are

and n is 0.

5. The compound according to claim 1, imidazo[1,2,-a]pyrimidine-2,3-dione,1,5,6,7-tetrahydro-6,6-dimethyl-1-{{p-(trifluoromethyl)-α-[p-trifluoromethyl)styryl]-cinnamylidene}amino}.

6. The compound according to claim 1, imidazo[1,2-a]pyrimidine-2,3-dione,1-{[p-chloro-α-(p-chlorostyryl)-cinnamylidene]amino}-1,5,6,7-tetrahydro-6,6-dimethyl- 7. The compound according to claim 1, imidazo[1,2-a]pyrimidine-2,3-dione,1-{[p-bromo-α-(p-bromostyryl)-cinnamylidene]amino}-1,5,6,7-tetrahydro-6,6-dimethyl- 8. The compound according to claim 1, imidazo[1,2-a]pyrimidine-2,3-dione,1-}[2-(p-chlorostyryl)-p-(trifluoromethyl)cinnamylidene]amino}-1,5,6,7-tetrahydro-6,6-dimethyl-.

9. The compound according to claim 1, imidazo[1,2-a]pyrimidine-2,3-dione,1,5,6,7-tetrahydro-6,6-dimethyl-1-{{p-(trifluoromethoxy)-α-[p-(trifluoromethoxy)-styryl]cinnamylidene}amino}-.

10. The compound according to claim 1, imidazo[1,2-a]pyrimidine-2,3-dione,1-{{p-(difluoromethylthio)-α-[p-(difluoromethylthio)styryl]cinnamylidene}amino}-1,5,6,7-tetrahydro-6,6-dimethyl-.

11. The compound according to claim 1, imidazo[1,2-a]pyrimidine-2,3-dione,1-{[p-isopropyl-α-(p-isopropyl)-styryl)cinnamylidene]-amino}-1,5,6,7-tetrahydro-6,6-dimethyl-.

12. The compound according to claim 1, 1H-imidazo[1,2-a]imidazole-2,3-dione,5,6-dihydro-1-{{p-trifluoromethyl)-α-[p-(trifluoromethyl)styryl]cinnamylidene}amino}-.

13. The compound according to claim 1, 1H-imidazo[1,2-a]imidazole-2,3-dione,5,6-dihydro-6-methyl-1-{{p-trifluoromethyl)-α-[p-(trifluoromethyl)styryl]-cinnamylidene}amino}-.

14. The compound according to claim 1, imidazo[1,2-a]pyrimidine-2,3-dione,1,5,6,7-tetrahydro-1-{{p-trifluoromethyl)-α-[p-(trifluoromethyl)styryl]cinnamylidene}amino}-.

15. The compound according to claim 1, 1H-imidazo[1,2-a][1,3]diazepine-2,3-dione,5,6,7,8-tetrahydro-1-{{p-(trifluoromethyl)-α-[p-(trifluoromethyl)-styryl]cinnamylidene}amino}-.

16. A method for controlling insects comprising: contacting the insects, their habitat, and/or their food supply, with an insecticidally effective amount of a compound having the structure:

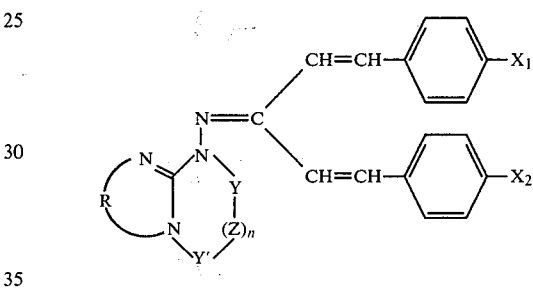

wherein R is a $C_2$–$C_4$ alkylene chain which may optionally be substituted with one or two $C_1$–$C_2$ alkyl group(s) or with one phenyl group; or —$CH_2$—CH=CH—$CH_2$—; $X_1$ and $X_2$ each are halogen, $CF_3$, $CHF_2O$, $CF_3O$, $CHF_2CF_2O$, $CHF_2S$, $C_1$–$C_3$ alkyl or; $C_1$–$C_3$ alkoxy; Y and Y' each is —$CH_2$— or

with the proviso that at least one of Y and Y' must be

Z is —$CH_2$— or —$C(CH_3)_2$—; and n is 0 or 1; and when n is 1, Y and Y' must be

17. The method according to claim 16, wherein $X_1$ and $X_2$ are both Cl, Br, $CF_3$ or $CF_3O$; R is

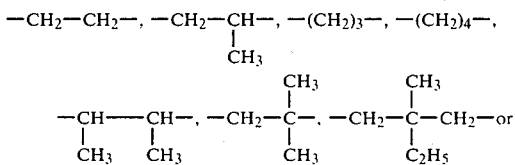

-continued

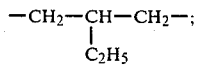

both Y and Y' are

and n is 0.

18. The method according to claim 16, wherein $X_1$ and $X_2$ are bromine, chlorine, iodine, $CF_3$, $CF_3O$, $CHF_2S$, $CHF_2CF_2O$ or; $C_2H_5$; R is

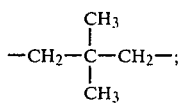

Y and Y' each are

and n is 0.

19. The method according to claim 16, wherein the insects are Lepidopterous insects, and the compound is applied at the rate of from 0.1 kg/hectare to 11.2 kg/hectare.

20. The method according to claim 16, wherein the insects are ants, family Formicidae, and the compound is applied at the rate of from 2.5 g/hectare to 37.5 g/hectare.

21. The method according to claim 16, wherein the insects are termites, cockroaches, grasshoppers, and ants, family Formicidae, and the compound is applied incorporated in a bait at a concentration of from 0.125% to 2.0% by weight.

22. The method according to claim 20, wherein the ants are the southern fire ant *Solenopsis xyloni,* the black imported fire ant *Solenopsis richteri* and the red imported fire ant *Solenopsis invicta.*

23. A method for protecting agronomic crops, trees, shrubs and ornamentals from attack by insects comprising applying to the crops an insecticidally effective amount of a compound represented by the structure:

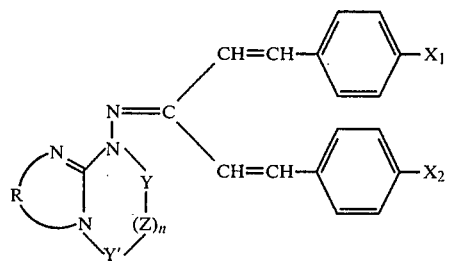

wherein R is a $C_2$-$C_4$ alkylene chain which may be substituted with one or two $C_1$-$C_2$ alkyl group(s) or with one phenyl group; or —$CH_2$—CH=CH—$CH_2$—; $X_1$ and $X_2$ each is halogen, $CF_3$, $CHF_2O$, $CF_3O$, $CHF_2CF_2O$, $CHF_2S$, $C_1$-$C_3$ alkyl or $C_1$-$C_3$ alkoxy; Y and Y' each is —$CH_2$— or

but at least one substituent must be

Z is —$CH_2$— or —$C(CH_3)_2$—; n is 0 or 1; and when n is 1, both Y and Y' must be

24. The method according to claim 23, wherein the insects are Lepidopterous insects, and the compound is applied at the rate of from 0.1 kg/hectare to 11.2 kg/hectare.

25. The method according to claim 23, wherein the insects are ants, family Formicidae, and the compound is applied at the rate of from 2.5 g/hectare to 37.5 g/hectare.

26. The method according to claim 25, wherein the ants are the southern fire ant *Solenopsis xyloni,* the black imported fire ant *Solenopsis richteri* and the red imported fire ant *Solenopsis invicta.*

* * * * *

UNITED STATES PATENT OFFICE
CERTIFICATE OF CORRECTION

Patent No. 4,322,422  Dated Mar. 30, 1982

Inventor(s) ROGER W. ADDOR and THOMAS W. DRABB, JR.

It is certified that error appears in the above-identified patent and that said Letters Patent are hereby corrected as shown below:

Column 1, lines 10 - 20, a double bond is missing between the ring carbon and the nitrogen; the structure should read as follows:

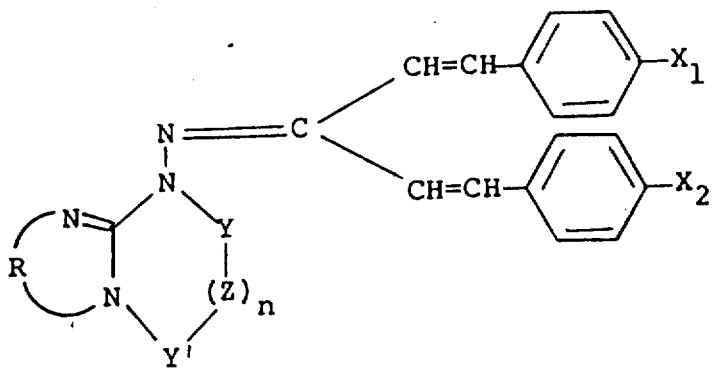

Column 2, line 34, cancel [1-2-3'-3].

Column 4, line 41, cancel [2] after "(trifluoromethyl)-" and in place thereof insert $\underline{a}$.

Column 7, line 8, cancel [(] after "-α-" and in place thereof insert $\underline{[}$.

Column 7, line 29, cancel [(] after "-α-" and in place thereof insert $\underline{[}$.

UNITED STATES PATENT OFFICE
CERTIFICATE OF CORRECTION

Patent No. 4,322,422                    Dated Mar. 30, 1982

Inventor(s) ROGER W. ADDOR and THOMAS W. DRABB, JR.

It is certified that error appears in the above-identified patent and that said Letters Patent are hereby corrected as shown below:

Column 11, line 4, cancel [P] after "[1,2-a]" and in place thereof insert p.

Column 11, line 15, cancel [-pyrimidinylhydrozone] and in place thereof insert pyrimidinylhydrazone.

Column 11, line 29, after " p-" insert (.

Column 11, line 33, after "[2-[-" insert 4-.

Signed and Sealed this

First Day of February 1983

[SEAL]

Attest:

GERALD J. MOSSINGHOFF

Attesting Officer    Commissioner of Patents and Trademarks